United States Patent [19]

Puy et al.

[11] Patent Number: 5,094,243
[45] Date of Patent: Mar. 10, 1992

[54] SUPPORT FOR AN ECHOGRAPHIC TRANSDUCER, IN PARTICULAR AN ECHOCARDIOGRAPHIC TRANSDUCER

[76] Inventors: Philippe Puy, 7, allée Claire-Fontaine, 30400 Villeneuve-les-Avignon; Alain Dreyer, Mas Desgrives, 84470 Chateauneuf-de-Gadagne, both of France

[21] Appl. No.: 544,060

[22] Filed: Jun. 22, 1990

Related U.S. Application Data

[63] Continuation of Ser. No. 307,090, Feb. 6, 1989, abandoned.

[30] Foreign Application Priority Data

Feb. 5, 1988 [FR] France .................... 88 01378

[51] Int. Cl.⁵ .................................... A61B 10/00
[52] U.S. Cl. ................................... 128/662.03
[58] Field of Search .......... 128/661.04, 662.03-662.06

[56] References Cited

U.S. PATENT DOCUMENTS

| | | | |
|---|---|---|---|
| 3,021,842 | 2/1962 | Flood | 128/303 B |
| 3,893,449 | 7/1975 | Lee et al. | 128/24 A X |
| 4,120,291 | 10/1978 | Paton et al. | 73/618 |
| 4,483,344 | 11/1984 | Atkov et al. | 128/662.03 |
| 4,526,169 | 7/1985 | Narishige et al. | 128/303 B |
| 4,757,823 | 7/1988 | Hofmeister et al. | 128/662.06 X |

FOREIGN PATENT DOCUMENTS 2735722  2/1979  Fed. Rep. of Germany .................... 128/662.04

Primary Examiner—Francis Jaworski
Attorney, Agent, or Firm—Blakely Sokoloff Taylor & Zafman

[57] ABSTRACT

The invention relates to a support for an echographic transducer, the support comprising a base (10), a transducer carrier (30), locking means (40) for locking the transducer carrier in position, and transducer carrier mounting means comprising two semi-circular hoops (20, 20') pivoting about mutually perpendicular axes (X, Y) extending in a common plane which is parallel to the plane of the base and which is situated in the proximity of the contact surface between the base and the body of the patient, each of said hoops having an elongate slot (21, 21') extending over the major portion of its length, and the transducer carrier being located at the intersection of the two slots. The invention is applicable to cardiac echography.

2 Claims, 2 Drawing Sheets

SUPPORT FOR AN ECHOGRAPHIC TRANSDUCER, IN PARTICULAR AN ECHOCARDIOGRAPHIC TRANSDUCER

This is a continuation of application Ser. No. 307,090 filed Feb. 6, 1989, and now abandoned.

The present invention relates to supports for echographic transducers, in particular echocardiographic transducers.

BACKGROUND OF THE INVENTION

Such supports are described, in particular, in French patents numbers 81 06 882 and 86 16 064, and in U.S. Pat. Nos. 3,893,449 and 4,483,344.

These supports serve to hold a transducer against a point on the body of a patient while enabling the angular position of the transducer axis to be adjusted to a certain extent relative to the surface with which the transducer is in contact.

The purpose of such angular positioning is to point the transducer towards the organ under examination, since it is not always possible to place the transducer immediately thereover.

Thus, when performing echocardiography, the practitioner begins by finding an intercostal window on the chest of the patient, after which the transducer is applied and pressed against said location, and finally the transducer is pointed so as to aim at the region of the heart to be examined by looking for the best viewing angle.

The above-mentioned patents describe a transducer support comprising:

a base having a contact surface suitable for being pressed against the body of a patient at the position which is to be examined;

a transducer carrier removeably receiving the transducer and provided with means for urging the transducer axially against the body of the patient;

means for mounting the transducer carrier on the base with the possibility of pointing the transducer carrier by pivoting; and locking means for locking the transducer carrier in position.

In practice, it is desirable for the transducer carrier to pivot about a point situated in the immediate proximity of the contact surface, as described in French patent 8106882 and the equivalent U.S. Pat. No. 4,483,344.

However, the support described in these two patents provide only a small degree of angular freedom for the transducer carrier about the normal to the plane of contact, and this can give rise to difficulties in some situations. This drawback is compensated to some extent by the fact that the transducer carrier is mounted on equipment which is moveable in translation along two perpendicular directions in order to change the point of contact without changing the position of the base, while the base is fixed to the patient's body by straps, however this gives rise to a transducer support whose mechanical structure is complex and the transducer cannot be changed quickly because that requires various parts of the transducer carrier to be disassembled.

One of the aims of the present invention is to provide a transducer support of the above-specified type which mitigates these drawbacks by providing for a very large degree of angular displacement relative to the normal to the contact plane, with rotation being performed about a fixed point which is as close as possible to the body of the patient.

SUMMARY OF THE INVENTION

Thus, according to the present invention:

the means for mounting the transducer carrier on the base comprise two semi-circular hoops pivotally mounted about respective mutually perpendicular axes extending in a common plane, which plane is parallel to the plane of the base and is situated in the proximity of the contact surface, each of said hoops having an elongate slot extending over the major portion of its length; and the transducer carrier is placed in both hoop slots where they intersect.

Advantageously:

the transducer carrier is substantially cylindrical in shape, thereby enabling the transducer to rotate about its own axis without moving the base or the hoops;

locking means comprise a nut disposed on a threaded portion of the transducer carrier, which portion projects outside the hoops, with tightening of said nut providing a single locking movement for fixing the hoop and transducer carrier assembly in position; and the transducer carrier is pointable within a cone having a 90° apex angle, with the axis of the cone being perpendicular to the contact surface.

BRIEF DESCRIPTION OF THE DRAWINGS

An embodiment of the invention is described by way of example with reference to the accompanying drawings, in which.

MORE DETAILED DESCRIPTION

Figure 1:
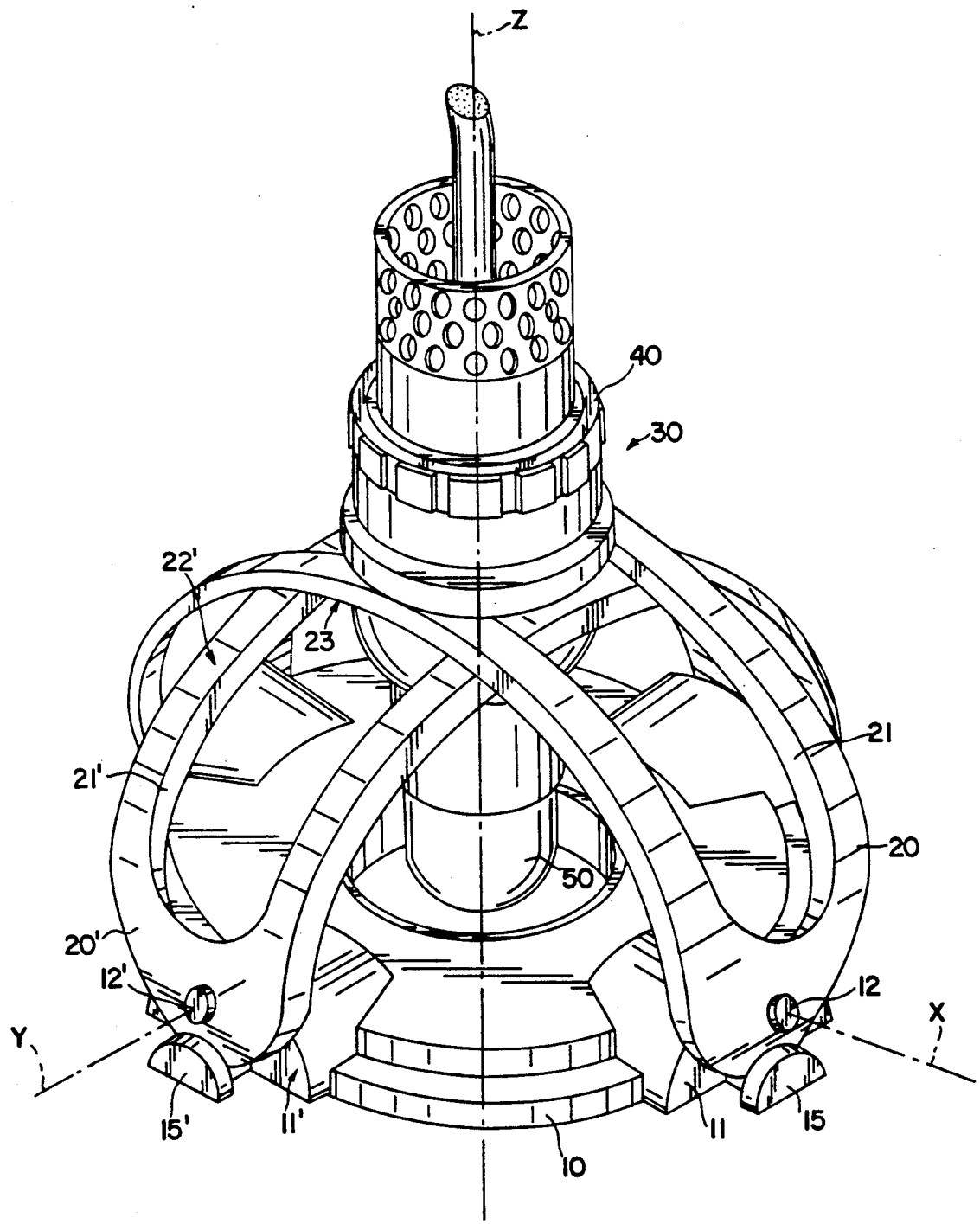
FIG. 1 is a perspective view of a transducer support in accordance with the invention and fitted with an echographic transducer.
Figure 2:
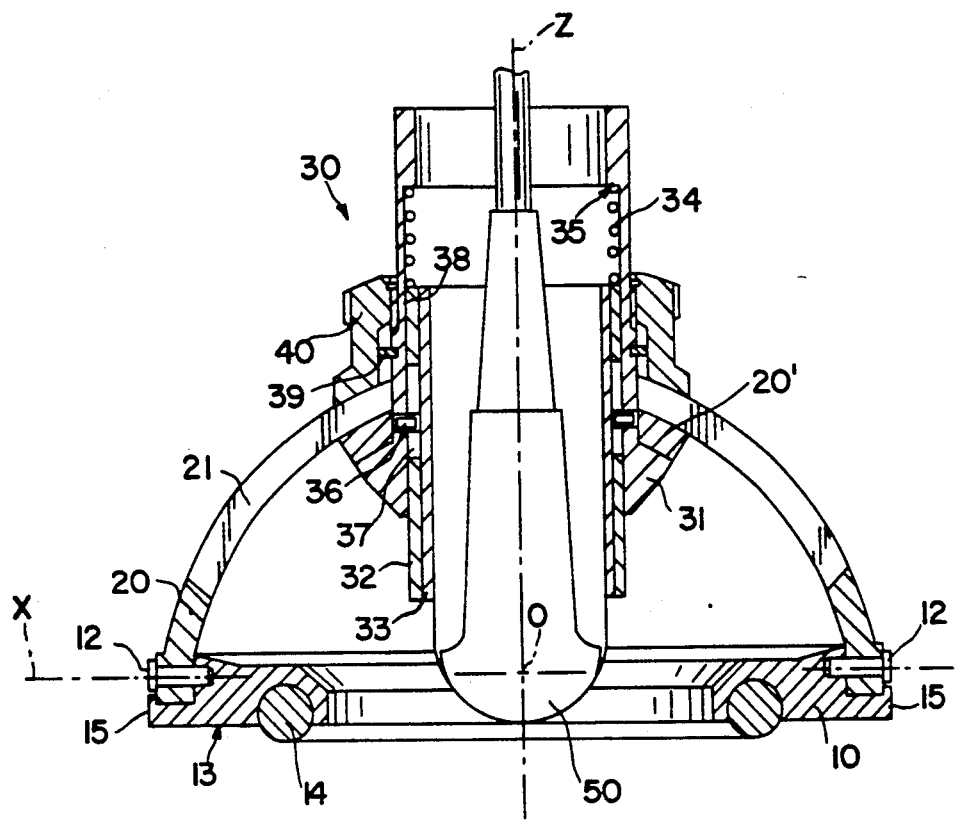
FIGS. 2 and 3 are sections in the plane XOZ of the FIG. 1 assembly, respectively showing the transducer pointing along the normal direction relative to the patient's body and pointing along a direction of maximum inclination.
Figure 3:
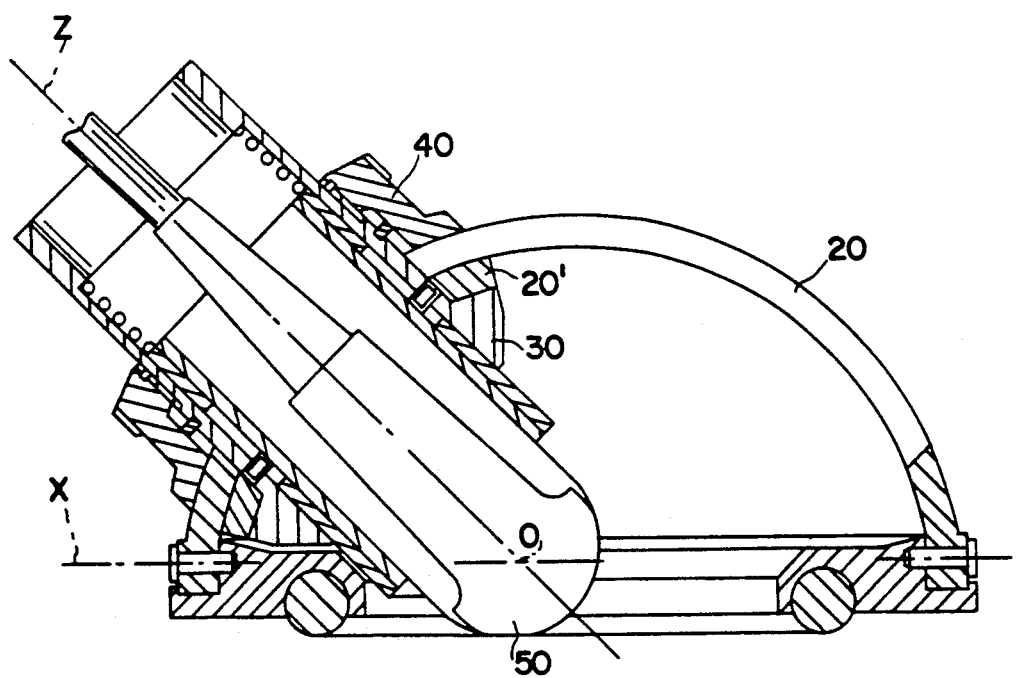

The figures show the transducer support constituted by items referenced 10 to 40 and serving to support an echographic transducer 50.

The transducer support comprises a base 10 which is substantially circular in shape having four flats 11, 11' disposed at right angles and receiving pins 12 and 12' lying on orthogonal X and Y axes.

These axes intersect at a point O situated at the center of the base and they extend in a common plane parallel to the contact surface 13 where the base is pressed against the body of the patient via an interposed pad 14, with said common plane being situated at a small distance from the surface 13.

The pins 12 and 12' support two moving hoops 20 and 20' of similar configuration, with the hoop 20 being slightly larger in size so as to pass over the hoop 20'. These hoops rock about the pins 12 and 12' respectively, with protective tongues 15 and 15' being provided on the base to prevent the hoops from rubbing against the body of the patient, which could hinder their rotation.

A major portion of the length of each hoop includes an elongate slot 21 or 21' with a transducer carrier 30 being placed through both of these slots where they intersect.

The top surface 22' of the bottom hoop 20' and the bottom surface 23 of the top hoop 20 are preferably identical hemispherical surfaces in order to enable the two hoops to move relative to each other without leaving play therebetween.

The transducer carrier 30 is provided with any suitable means for receiving the transducer in the transducer carrier. For example, these means may comprise a body 31 receiving a cylindrical sheath 32 which is in turn provided with an internal sleeve 33 for clamping the transducer 50 in position. The sheath 32, and thus the transducer 50, is resiliently urged downwards by a spring 34 inserted inside the transducer carrier between the sheath 32 and an inwardly directed shoulder 35 on the body 31 of the transducer carrier.

In addition, the sheath 32 is prevented from rotating (about the longitudinal axis Z of the transducer) by means of pegs 36 fixed to the body of the transducer carrier 31 and cooperating with grooves 37 formed in the periphery of the sheath 32 and running parallel to the axis Z.

The body 31 also has a threaded portion 38 on its outside surface where it projects outside the hoops 20 and 20' for receiving a knurled nut 40 enabling the position of the assembly to be firmly locked in place once the desired angular position has been found. When the nut is loosened, the body of the transducer carrier is held in place on the hoops by means of a spring clip 39.

This configuration makes it possible to lock the assembly in position without disassembling the transducer carrier in any way and by means of a single clamping movement.

The transducer is fixed in the apparatus by being inserted from above and it is held in place by means of the sleeve, thereby enabling the transducer to be removed while maintaining the locking means in the clamped position, i.e. without disassembling the transducer carrier or spoiling its adjustment.

In addition, the system for holding the transducer using a sleeve makes it possible to make direct use of transducers of different diameters without fitting an intermediate spacer, with the maximum diameter merely being designed to be capable of receiving the largest diameter transducers.

Finally, the system is easy for a practitioner to handle using only one hand since the practitioner needs only to loosen the nut 40 a little to find the optimum examination angle, and then to tighten the nut 40 once said position has been reached. While the angular position of the transducer is being adjusted, the transducer pivots about the point O, i.e. its center of rotation is practically the same as the point of contact between the transducer and the patient's body.

Finally, it is easy during examination to raise the transducer a little in order to place a contact gel on the end thereof without dismantling the base or the transducer carrier, and the transducer is then returned to exactly the same position as it occupied previously.

We claim:

1. A support for an echographic transducer comprising:
    a base having a contact surface lying in a plane suitable for being pressed against the body of a patient at a position which is to be examined;
    a substantially cylindrically shaped transducer carrier for removably receiving the transducer and provided with means for urging the transducer axially against the body of the patient, said transducer carrier comprising a sheath which is open at its top end in order to receive the transducer without separating the base from the body of the patient, said sheath being provided with an inside sleeve for positioning the transducer inside the transducer carrier;
    means for mounting the transducer carrier on the base and for pointing the transducer carrier by pivoting it about a point situated in the proximity of the contact surface and for rotating about said point in a first plane and in a second plane perpendicular to said first plane, said means for mounting comprising two semicircular hoops having an elongate slot extending over the major portion of their length and pivotally mounted about respective mutually perpendicular axes extending in a common plane, said plane being substantially parallel to the plane of the base; and
    locking means for locking the transducer carrier in position, said locking means comprising a nut disposed on a treaded portion of the transducer carrier projecting outside the hoops such that tightening of said nut provides a single locking movement for fixing the hoops and transducer carrier in position;
    wherein:
    the transducer carrier is placed in both hoop slots where they intersect, and the transducer can be placed into said sheath without changing the adjustment of said hoops.

2. A transducer support according to claim 1, in which the transducer carrier is pointable within a cone having a 90° apex angle, with the axis of the cone being perpendicular to the contact surface.

* * * * *